United States Patent [19]

Goodman

[11] Patent Number: 4,857,491

[45] Date of Patent: Aug. 15, 1989

[54] VISCOSIFYING ALCOHOLIC MEDIA

[75] Inventor: Howard Goodman, St. Austell, England

[73] Assignee: ECC International Limited, Great Britain

[21] Appl. No.: 896,396

[22] Filed: Aug. 13, 1986

[30] Foreign Application Priority Data

Aug. 15, 1985 [GB] United Kingdom ............... 8520463

[51] Int. Cl.[4] .................. C04B 14/00; C04B 33/00
[52] U.S. Cl. .................... 501/148; 501/146; 106/504; 106/484; 106/487; 106/468; 106/481; 106/491
[58] Field of Search ............... 501/146, 148; 106/287.17, 308 Q, 308 N

[56] References Cited

U.S. PATENT DOCUMENTS

| | | | |
|---|---|---|---|
| 2,966,506 | 12/1960 | Jordan | 260/448 C |
| 4,469,639 | 9/1984 | Thompson et al. | 260/448 C |
| 4,517,112 | 5/1985 | Mardis et al. | 106/287.17 |
| 4,569,923 | 2/1986 | Knudson, Jr. et al. | 501/148 |
| 4,623,398 | 11/1986 | Goodman et al. | 501/148 X |
| 4,631,091 | 12/1986 | Goodman | 106/308 N |

FOREIGN PATENT DOCUMENTS

| | | | |
|---|---|---|---|
| 147233 | 3/1981 | German Democratic Rep. | 501/148 |
| 53-16039 | 2/1978 | Japan | 106/308 Q |
| 2158053 | 11/1985 | United Kingdom | 501/146 |

OTHER PUBLICATIONS

Clay Mineralogy, R. E. Grim, Second Edition, McGraw-Hill, 1968, pp. 51, 57-59 and 77-80.

*Primary Examiner*—William R. Dixon, Jr.
*Assistant Examiner*—Karl Group
*Attorney, Agent, or Firm*—Klauber & Jackson

[57] ABSTRACT

An organo-clay is prepared by treating a clay mineral of the smectite type with a mixture of di(lower alkyl) arylkyl (higher alkyl) ammonium compound and a di(lower alkyl) di(higher alkyl) ammonium compound and thereafter subjecting the treated clay mineral to high shear mixing for a time sufficient to dissipate in the mixture at least 100 KJ of energy per Kg of dry solids in the mixture. The organo-clay is useful in gelling compositions containing one or more liquid aliphatic alcohols.

6 Claims, No Drawings

VISCOSIFYING ALCOHOLIC MEDIA

This invention relates to a method of increasing the viscosity of liquid compositions containing significant amounts of aliphatic alcohols and, more particularly, is concerned with organo-clays and their use in forming gels with alcoholic media.

BACKGROUND OF THE INVENTION

Many compositions used for cosmetic or personal hygiene purposes comprise a suspension or solution of active ingredients in an aliphatic alcohol having from 1 to 4 carbon atoms. Most commonly the aliphatic alcohol used is ethanol as it is readily available, relatively inexpensive and has no adverse properties. In many cases such compositions are required to be in the form of a thixotropic gel, rather than a freeflowing liquid, in order to facilitate topical application to the human body. A typical example of such a composition is underarm deodorant which must be capable of being mixed by shaking but must not be too freeflowing on application. Hitherto the viscosity of such compositions has been increased by incorporating into the alcoholic medium an organo-clay which has been prepared by surface treating a clay mineral of the smectite type with a quaternary alkyl ammonium compound of the type wherein at least one of the alkyl groups is a higher alkyl group containing from 10 to 24 carbon atoms and wherein at least one of the remaining three alkyl groups is a lower alkyl group containing less than 10 carbon atoms. In general, it has been found that in order to achieve the desired viscosifying effect it is necessary to add at least 10% by weight, based on the weight of the alcoholic medium, of an organo-clay surface treated with a quaternary alkyl ammonium compound. One attempt which has been made to overcome the need to use such relatively large amounts of the organo-clay is disclosed in British Patent Specification No. 2,001,063A.

SUMMARY OF THE INVENTION

According to the present invention there is provided an organo-clay which has been prepared by treating a clay mineral of the smectite type with a mixture of a di(lower alkyl) aralkyl (higher alkyl) ammonium compound and a di(lower alkyl) di(higher alkyl) ammonium compound and thereafter subjecting the treated clay mineral to high shear mixing for a time sufficient to dissipate in the mixture at least 100 KJ of energy per Kg of dry solids in the mixture.

Generally, the mole ratio of said di(lower alkyl) aralkyl (higher alkyl) ammonium compound to said di(lower alkyl) di(higher alkyl) ammonium compound in said mixture will be in the range of from 99:1 to 20:80, and preferably will be in the range 90:10 to 35:65.

Preferably, the lower alkyl group of each of the quaternary ammonium compounds has from 1 to 3 carbon atoms.

Preferably, the higher alkyl group and/or aralkyl group of the quaternary ammonium compound has from 10 to 24 carbon atoms. Advantageously, the higher alkyl group is derived from a natural fatty material, such as tallow, which comprises alkyl groups having from 12 to 20 carbon atoms but in which $C_{18}$ groups predominate. A typical analysis of such a mixture of hydrocarbon radicals contained in tallow is:

$C_{12}$ 1.0%, $C_{14}$ 4.5%, $C_{15}$ 0.5%, $C_{16}$ 30.5%, $C_{17}$ 1.5%, $C_{18}$ 62%.

The hydrocarbon radicals may be partially unsaturated, as in natural tallow, or may be substantially completely saturated as a result of treating the tallow with hydrogen in the presence of a suitable catalyst.

In a prepared embodiment of the invention, the clay mineral of the smectite type is treated with a mixture of (a) a dimethyl di(higher alkyl) ammonium compound and (b) a dimethyl benzyl (higher alkyl) ammonium compound in which the quaternary ammonium compounds (a) and (b) are used mixed together in molar ratios in the range of from 1:99 to 80:20, and most preferably in molar ratios in the range of from 10:90 to 65:35.

Clay minerals of the smectite type include bentonite, montmorillonite, hectorite, saponite and the like.

The high shear mixing is advantageously caried out for a time such that at least 400 KJ of energy per Kg of dry solids have been dissipated in the mixture, and preferably is effected by passing the suspension through a homogeniser of the type in which the suspension is forced in the form of a film edgewise through a thin, hard surfaced gap under a pressure of at least 250 pounds per square inch (1.7 MPa) and at high viscosity. A suitable homogeniser is described in British Pat. Specification No. 987,176 (or in U.S. Pat. Nos. 3,039,703 and 3,162,379). Such a homogeniser is manufactured by the Manton-Gaulin Company. Advantageously the homogeniser is operated at a pressure of at least 1500 pounds per square inch (10.5 MPa). The amount of energy, in KJ per Kg of dry solids, dissipated in the mixture is given by the expression:

$$E = \frac{nP \cdot 10^3}{w}$$

where P is the pressure in MPa exerted in the Manton-Gaulin homogeniser, n is the number of passes through the Manton-Gaulin homogeniser, and w is the weight in grams of dry solids in 1 liter of the aqueous mixture.

Preferably, the clay mineral is suspended in water and the suspension mixed with the mixture of quaternary ammonium compounds in proportions such that there are present from 95 to 140 milliequivalents of quaternary ammonium cation per 100g of dry clay mineral. Most preferably the proportions are such that there are present from 100 to 120 milliequivalents of quaternary ammonium cation per 100g of dry clay mineral.

The amount of organo-clay incorporated into the alcoholic medium is conveniently from 1% to 10% by weight, based on the weight of the alcoholic medium (i.e. alcohol and water if any water is present). Normally about 5% by weight of organo-clay is found to be sufficient. In general, less organo-clay is required to give a certain gelling effect if water is present than if the alcoholic medium is anhydrous.

The present invention is illustrated by the following Example.

EXAMPLE

Organo-clay samples were prepared by the following method:

An aqueous suspension of bentonite was prepared by mixing a raw Wyoming sodium bentonite in a blunger with sufficient water to form a suspension containing 10% by weight of dry clay. The suspension thus formed was passed through a No. 300 mesh British Standard sieve (nominal aperture 0.053mm) and the undersize fraction was diluted with water to about 6% by weight of solids and then subjected to a particle size separation in a nozzle discharge, disc centrifuge at a flow rate of 1 liter per minute. The fine fraction, which had a solids content of 4% by weight, was passed once through a Manton-Gaulin homogeniser at a pressure of 4000 psi (27.6 MPa). The energy dissipated in the suspension in the homogeniser was 673 KJ per Kg of dry bentonite. The product from the homogeniser was divided into three portions A, B and C which were further treated by the following methods:

PORTION A

A mixture was prepared containing dimethyl di(hydrogenated tallow) ammonium chloride (2M2HT) and dimethyl benzyl(hydrogenated tallow) ammonium chloride (2MBHT) in a 50:50 molar ratio. Both quaternary ammonium compounds are available commercially in suspension in isopropyl alcohol.

That weight of the mixture of quaternary ammonium compounds which was calculated to provide 105 milliequivalents of quaternary ammonium compound per 100g of dry clay mineral was melted and poured into 1 Kg of the aqueous suspension of refined bentonite prepared as described above at a temperature of 65° C. The resultant mixture was then passed twice through the Manton-Gaulin homogeniser at a pressure of 4000 psi (27.6 MPa), there being dissipated in the mixture 899 KJ of energy per Kg of dry solids in the mixture. The mixture was filtered on a Buchner funnel, washed with hot water and dried for 16 hours at 60 ° C. in an air-swept oven. The dry product was then milled to pass through a sieve of nominal aperture 0.080 mm.

PORTION B

This was prepared in the manner described under Portion A above except that, in place of the treatment in the Manton-Gaulin homogeniser, the mixture of the aqueous suspension of refined bentonite and the quaternary ammonium compounds was mixed for half an hour by means of a paddle mixer.

PORTION C

This was prepared in the manner described under Portion A above except that, in place of the mixture of 2M2HT and 2MBHT, there was used a weight of 2MBHT which was calculated to provide 105 milliequivalents of quaternary ammonium compound per 100g of dry clay mineral. In this case there was dissipated in the mixture in the Manton Gaulin homogeniser 948 KJ of energy per Kg of dry solids in mixture.

Suspensions containing 5% by weight of each of organo-clays A, B and C in absolute ethanol were prepared, the organo-clay being mixed with the ethanol by means of a Cowles Blade rotating at 3000 rpm for 10 minutes. The viscosity of each suspension was then measured by means of a Brookfield Viscometer using Spindle No. 2 rotating at speeds of 1 rpm, 20 rpm and 50 rpm.

As a comparison the experiments were repeated using commercially available organo-clays D to J.

The results obtained are set forth in the following Table.

TABLE

| Organoclay | Quaternary ammonium compound | Milliequivalents per 100 g of dry clay | Whether organo-clay treated in homogeniser | Viscosity (mPa.s) | | |
|---|---|---|---|---|---|---|
| | | | | 1 rpm | 20 rpm | 50 rpm |
| A | 50% 2M2HT / 50% 2MBHT | 105 | yes | 2000 | 375 | 160 |
| B | 50% 2M2HT / 50% 2MBHT | 105 | no | 750 | 75 | 40 |
| C | 2MBHT | 105 | yes | 700 | 50 | 24 |
| D | 2M2HT | 95 | no | too low to measure | | |
| E | 2M2HT | 95 | yes | too low to measure | | |
| F | 2M2HT | 130 | yes | too low to measure | | |
| G | 75% 2M2HT / 25% 2MBHT | 100 | no | too low to measure | | |
| H | 2M2HT | 100 | no | too low to measure | | |
| I | MB2HT + anionic surfactant | 150 | no | too low to measure | | |
| J | 2MBHT + anionic surfactant | 150 | no | too low to measure | | |

These results show that none of the commercially-available organo-clays D to J was able to provide a sufficiently high viscosity when used at 5% by weight in the absolute ethanol and that a good result was obtained only when there was used a mixture of organo-clays in accordance with the invention, e.g. organo-clay A.

I claim:

1. A thixotropic liquid composition containing a significant amount of one or more aliphatic alcohols having from 1 to 4 carbon atoms and containing from 1% to 10% by weight, based on the weight of the aliphatic alcohol, of an organo-clay which has been prepared by treating a smectite clay mineral with a mixture of a di(lower alkyl) aralkyl (higher alkyl) ammonium compound and a di(lower alkyl) di(higher alkyl) ammonium compound wherein the higher alkyl group of each of the quaternary ammonium compound contains from 10 to 24 carbon atoms and the lower alkyl group of each of the quaternary ammonium compounds contains less than 10 atoms; the mole ratio of said di(lower alkyl) aralkyl (higher alkyl) ammonium compound to said di(lower alkyl) di(higher alkyl) ammonium compound in said mixture being in the range of from 99:1 to 20:80; said clay mineral being suspended in water and the suspension thus formed mixed with the said mixture of ammonium compounds in proportions such that there are present from 95 to 140 milliequivalents of quaternary ammonium cation per 100 g of dry clay material; and thereafter subjecting the treated clay mineral to high shear mixing for a time sufficient to dissipate in the mixture at least 100 kJ of energy per kg of dry solids in the mixture.

2. A liquid composition according to claim 1, wherein the lower alkyl group of each of the quaternary ammonium compounds has from 1 to 3 carbon atoms.

3. A liquid composition according to claim 1, wherein the smectite clay mineral is treated with a mixture of (a) a dimethyl di(higher alkyl) ammonium compound and (b) a dimethyl benzyl (higher alkyl) ammonium compound.

4. A liquid composition as claimed in claim 1, wherein the smectite clay mineral is treated with a mixture of (a) a dimethyl di(hydrogenated tallow) ammonium compound and (b) a dimethyl benzyl (hydrogenated tallow) ammonium compound.

5. A liquid composition as claimed in claim 1, wherein the treated clay mineral is subjected to high shear mixing for a time sufficient to dissipate in the mixture at least 400 kJ of energy per kg of dry solids in the mixture.

6. A liquid composition as claimed in claim 1, wherein the mole ratio of said di(lower alkyl) aralkyl (higher alkyl) ammonium compound to said di(lower alkyl) di(higher alkyl) ammonium compound in said mixture is in the range of from 90:10 to 35:65.

* * * * *